US012154285B2

(12) United States Patent
Schaefferkoetter

(10) Patent No.: US 12,154,285 B2
(45) Date of Patent: Nov. 26, 2024

(54) DEEP LEARNING FOR REGISTERING ANATOMICAL TO FUNCTIONAL IMAGES

(71) Applicant: Siemens Medical Solutions USA, Inc., Malvern, PA (US)

(72) Inventor: Joshua Schaefferkoetter, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 395 days.

(21) Appl. No.: 17/651,246

(22) Filed: Feb. 16, 2022

(65) Prior Publication Data

US 2023/0260141 A1 Aug. 17, 2023

(51) Int. Cl.
*G06T 7/00* (2017.01)
*G06T 7/33* (2017.01)

(52) U.S. Cl.
CPC ............ *G06T 7/33* (2017.01); *G06T 7/0012* (2013.01); *G06T 2207/10081* (2013.01); *G06T 2207/10088* (2013.01); *G06T 2207/10104* (2013.01); *G06T 2207/10108* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | | |
|---|---|---|---|---|
| 8,818,057 | B2 * | 8/2014 | Bond | G16H 30/20 382/128 |
| 2003/0216631 | A1 * | 11/2003 | Bloch | G06T 3/153 600/407 |
| 2020/0184660 | A1 * | 6/2020 | Shi | G06T 7/30 |
| 2020/0289077 | A1 * | 9/2020 | Bai | A61B 6/584 |
| 2020/0381096 | A1 * | 12/2020 | Zaharchuk | G06F 18/24323 |
| 2021/0158142 | A1 * | 5/2021 | Luo | G06N 3/045 |

FOREIGN PATENT DOCUMENTS

| | | | | |
|---|---|---|---|---|
| CN | 109523584 | | 3/2019 | |
| CN | 111210465 | | 5/2020 | |
| CN | 111210465 | A * | 5/2020 | ............... G06T 7/33 |
| WO | 2016165034 | | 10/2016 | |

OTHER PUBLICATIONS

Balakrishnan, G., et al., Voxelmorph: a learning framework for deformable medical image registration. IEEE transactions on medical imaging, 2019. 38(8): p. 1788-1800.

(Continued)

*Primary Examiner* — Dung D Tran

(57) ABSTRACT

A framework for registering anatomical to functional images using deep learning. In accordance with one aspect, the framework extracts features by applying an anatomical image and a corresponding functional image as input to a first trained convolutional neural network. A deformation field is estimated by applying the extracted features as input to a second trained convolutional neural network. The deformation field may then be applied to the anatomical image to generate a registered anatomical image.

20 Claims, 8 Drawing Sheets

(56) References Cited

OTHER PUBLICATIONS

Boveiri, H.R., et al., Medical image registration using deep neural networks: A comprehensive review. Computers & Electrical Engineering, 2020. 87: p. 106767.

Cao, X., et al. Deep learning based inter-modality image registration supervised by intra-modality similarity, in International workshop on machine learning in medical imaging. 2018. Springer.

Chee, E. and Z. Wu, Airnet: Self-supervised affine registration for 3d medical images using neural networks. arXiv preprint arXiv:1810.02583, 2018.

Chen, M., et al., Cross contrast multi-channel image registration using image synthesis for MR brain images. Medical image analysis, 2017. 36: p. 2-14.

De Vos, B.D., et al., A deep learning framework for unsupervised affine and deformable image registration. Medical image analysis, 2019. 52: p. 128-143.

Fu, Y., et al., Deep learning in medical image registration: a review. Physics in Medicine & Biology, 2020. 65(20): p. 20TR01.

Jaderberg, M., K. Simonyan, and A. Zisserman, Spatial transformer networks. Advances in neural information processing systems, 2015. 28: p. 2017-2025.

Kang, H., et al., An optimized registration method based on distribution similarity and DVF smoothness for 3D PET and CT images. IEEE Access, 2019. 8: p. 1135-1145.

Kingma, D.P. and J. Ba, Adam: A method for stochastic optimization. arXiv preprint arXiv: 1412.6980, 2014.

Ronneberger, O., P. Fischer, and T. Brox. U-net: Convolutional networks for biomedical image segmentation. in International Conference on Medical image computing and computer-assisted intervention. 2015. Springer.

Roy, S., et al. MR to CT registration of brains using image synthesis. in Medical Imaging 2014: Image Processing. 2014. International Society for Optics and Photonics.

Xiao, H., G. Ren, and J. Cai, A review on 3D deformable image registration and its application in dose warping. Radiation Medicine and Protection, 2020.

Yu, H., et al., Unsupervised 3D PET-CT image registration method using a metabolic constraint function and a multi-domain similarity measure. IEEE Access, 2020. 8: p. 63077-63089.

Dey Joyoni et al: "Multi-modal rigid and non-rigid registration for attenuation correction in cardiac SPECT/CT using emission scatter to CT conversion", 2012 IEEE Nuclear Science Symposium and Medical Imaging Conference Record, Oct. 1, 2012, pp. 2859-2866.

Extended European Search Report for Corresponding EP Application No. 23156992.2, mailed Apr. 13, 2023.

\* cited by examiner

DEEP LEARNING FOR REGISTERING ANATOMICAL TO FUNCTIONAL IMAGES

TECHNICAL FIELD

The present disclosure generally relates to digital medical image data processing, and more particularly to registering anatomical images to functional images using deep learning.

BACKGROUND

Hybrid imaging plays an important role in accurately identifying diseased and normal tissues. Hybrid imaging provides combined benefits by fusing images acquired by different modalities. For example, anatomical imaging (e.g., Computed Tomographic or CT, Magnetic Resonance or MR) provides structural details, while functional imaging (e.g., Positron Emission Tomographic or PET, single-photon emission computed tomography or SPECT) provides insight into biological behaviors, such as changes in metabolism, blood flow, regional chemical composition or absorption. The complementarity between anatomical and functional imaging modalities has provided physicians a means to achieve unprecedented levels of diagnostic accuracy, accelerating the adoption of functional imaging in the clinical setting.

This also introduces a new paradigm for correcting emission images. Since annihilation photons arise from within the imaging subject, they can be absorbed and/or scattered by the physical mass of the subject before being detected. This results in attenuation of the PET signal, a phenomenon which affects a significant portion of the data that must be accounted for in order to produce accurate images. Before PET/CT, a map of linear attenuation coefficients (i.e., mu map) was usually measured by rotating an external positron-emitting rod or line source of known activity around the subject prior to the PET acquisition. This approach added additional time to the total scanning session, was susceptible to gross subject motion and produced only a low-resolution estimate.

In hybrid PET imaging systems, anatomical images (e.g., CT or MR) may be used to correct raw PET acquisition data for attenuation and scatter. The anatomical images provide a measurement of photon attenuation in the subject that can be used to directly generate a PET mu map by scaling from X-ray tube to photon annihilation energies. This CT-based attenuation correction (AC) provides a high-quality correction in a very short time. Moreover, the "simultaneity" of the anatomical and functional data acquisitions has thus far mitigated the need to spatially co-register the multimodal images.

However, these acquisitions are in fact not purely simultaneous, and the previous point depends on the assumption of no inter-scan subject movement. Unfortunately, this is often not true; slight differences in scanning time points leave the possibility for subject movement between scans. Spatial misalignments can be caused by gross subject movement and involuntary physiological motion. For example, a standard whole-body (WB) PET scan is several minutes long and captures the activity distribution averaged over the subject's breathing cycle. It is common to observe quantitative errors because the CT is acquired at a different respiratory phase. Moreover, for physiologically gated images, it is impossible for a single CT to provide accurate corrections for every PET frame.

Subject misalignment between the functional and anatomical imaging leads to errors in the quantification, and causes obvious qualitative problems with reconstructed PET images, significantly deteriorating the accuracy of the PET corrections. FIG. 1 shows a reconstructed PET image 102 of a subject with artifacts indicated by arrows 106a-c at multiple locations. The artifacts are produced due to quantification errors resulting from misaligned PET and CT data. More particularly, characteristic "banana" artifacts 106a and 106b resulted from gross patient motion in the head and arm respectively. Artifact 106c produced at the liver dome resulted from respiratory motion. Since this subject had clear artifacts arising from different types of motion at multiple locations (indicated by the arrows), it could not be included in a training set and was used only for validation. These errors are ubiquitous in hybrid PET imaging, but are typically ignored since there are currently no robust methods to match the CT image to the PET image.

SUMMARY

Described herein is a framework for registering anatomical to functional images using deep learning. In accordance with one aspect, the framework extracts features by applying an anatomical image and a corresponding functional image as input to a first trained convolutional neural network. A deformation field is estimated by applying the extracted features as input to a second trained convolutional neural network. The deformation field may then be applied to the anatomical image to generate a registered anatomical image.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
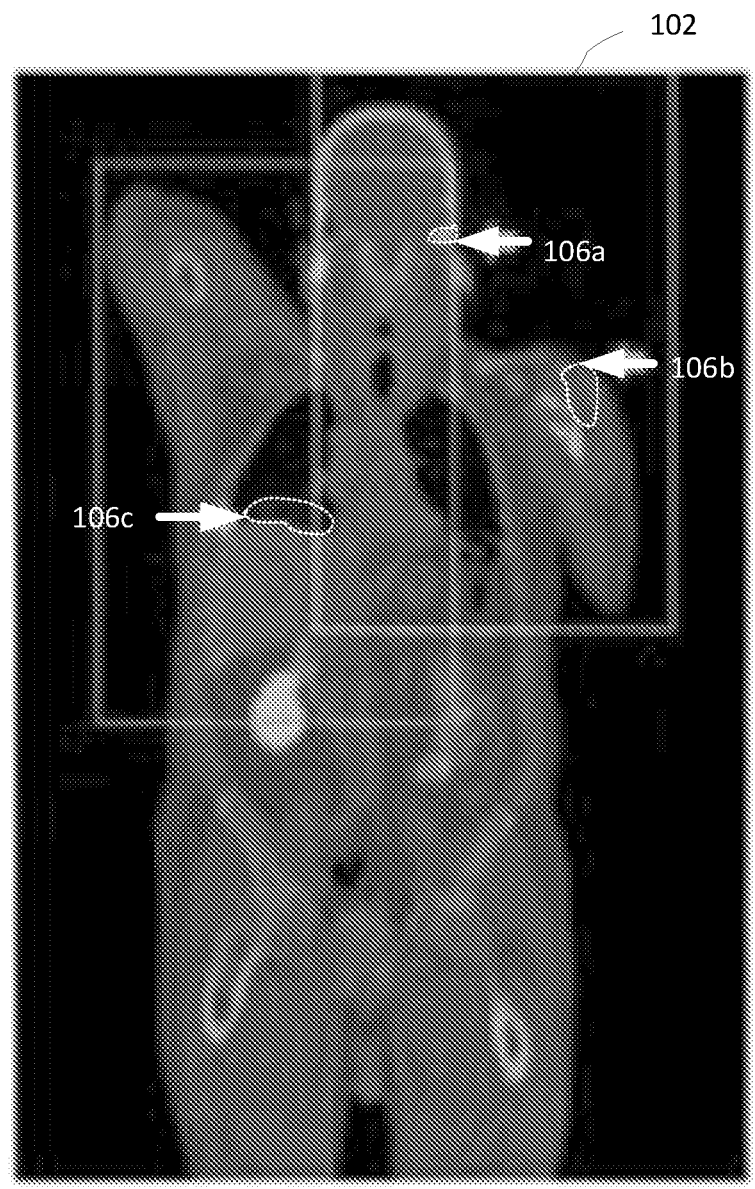
FIG. 1 shows a reconstructed PET image of a subject with artifacts at multiple locations.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to high-resolution computed tomography (HRCT), x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

For most clinical imaging protocols, the problem of subject misalignment has not been solved but simply ignored, since no good solution exists. There are some specific applications in which corrections are applied to address spatial misalignments. For example, in cardiac perfusion studies, mis-registration due to respiratory motion can lead to regions of artificial photopenia in the reconstructed PET images. These regions may be perceived as myocardial defects. This is currently addressed by simply translating the anatomical image in X, Y and Z dimensions so that the heart is aligned between the two images. Such approach does offer improvements, but can be tedious and/or time-consuming. Furthermore, even good translational registration for the heart does not guarantee accurate quantification at other locations. A technique to accurately correct the spatial alignment at every point in the field-of-view, i.e., elastic registration, may offer substantial benefits over current methods.

Similar elastic registration may possibly be performed using conventional methods that iteratively update a transformation until some similarity metric between the two images is optimized. Conventional methods, however, are time consuming. Furthermore, this iterative optimization approach is often unreliable, resulting in chaotic behavior. This is especially true for inter-modal registration in which pixel values are not correlated. Techniques based on deep learning are potentially more reliable, reproducible and can be performed in a fraction of the time.

The present framework provides a system and method for anatomical to functional image registration using a deep learning technique. More particularly, one aspect of the framework reliably optimizes or elastically warps an anatomical image for correcting functional images. The present deep learning technique derives a motion deformation field between the functional image and its corresponding anatomical image. The deformation field may be represented by a dense finely-sampled displacement matrix that can be used to warp the anatomical image to match the spatial distribution of the functional tracer. The warped anatomical image may then be used for downstream functional image corrections.

This method has the potential to improve the quantitative accuracy of the reconstructed images. A very fast three-dimensional (3D) elastic registration (typically just a few seconds) between functional and anatomical images may be performed using the present framework. The network architecture and training methodology yield a robust method with no (or minimal) additional hardware requirements. The quantitative impact on PET reconstruction has been evaluated in a population of clinical patients with various PET tracers, and a substantial reduction in reconstructed motion-induced artifacts was observed. Furthermore, the efficacy of this method has been demonstrated for correcting spatial inconsistencies due to both physiological and bulk subject motion. The applicability of this approach has been demonstrated for general whole body (WB) imaging and cardiac perfusion studies. It should be appreciated, however, that the present framework may also be applied to other types of studies.

This framework was found to improve misregistration artifacts at various sites across the whole body in the validation datasets. Most notably, these artifacts include respiratory effects occurring near the lung/liver border, which are ubiquitous in conventional PET imaging. Warping the anatomical image data so that the morphological boundaries were aligned with the distribution of the PET activity was found to substantially reduce the corresponding "banana" artifacts in test subjects. Misalignment artifacts due to gross involuntary motion were also found to benefit from this approach.

The present framework may also be used for scanning applications, such cardiac perfusion studies. For example, if respiratory motion causes mu map misalignment, it is possible that the activity in the myocardium is under-corrected in the reconstructed PET images, thereby producing apparent perfusion defects and false positive findings. This is a significant clinical consideration, and a robust method to optimize the attenuation correction (AC) for the PET data can help standardize this task. These and other exemplary features and advantages will be described in more detail herein.

Figure 2:
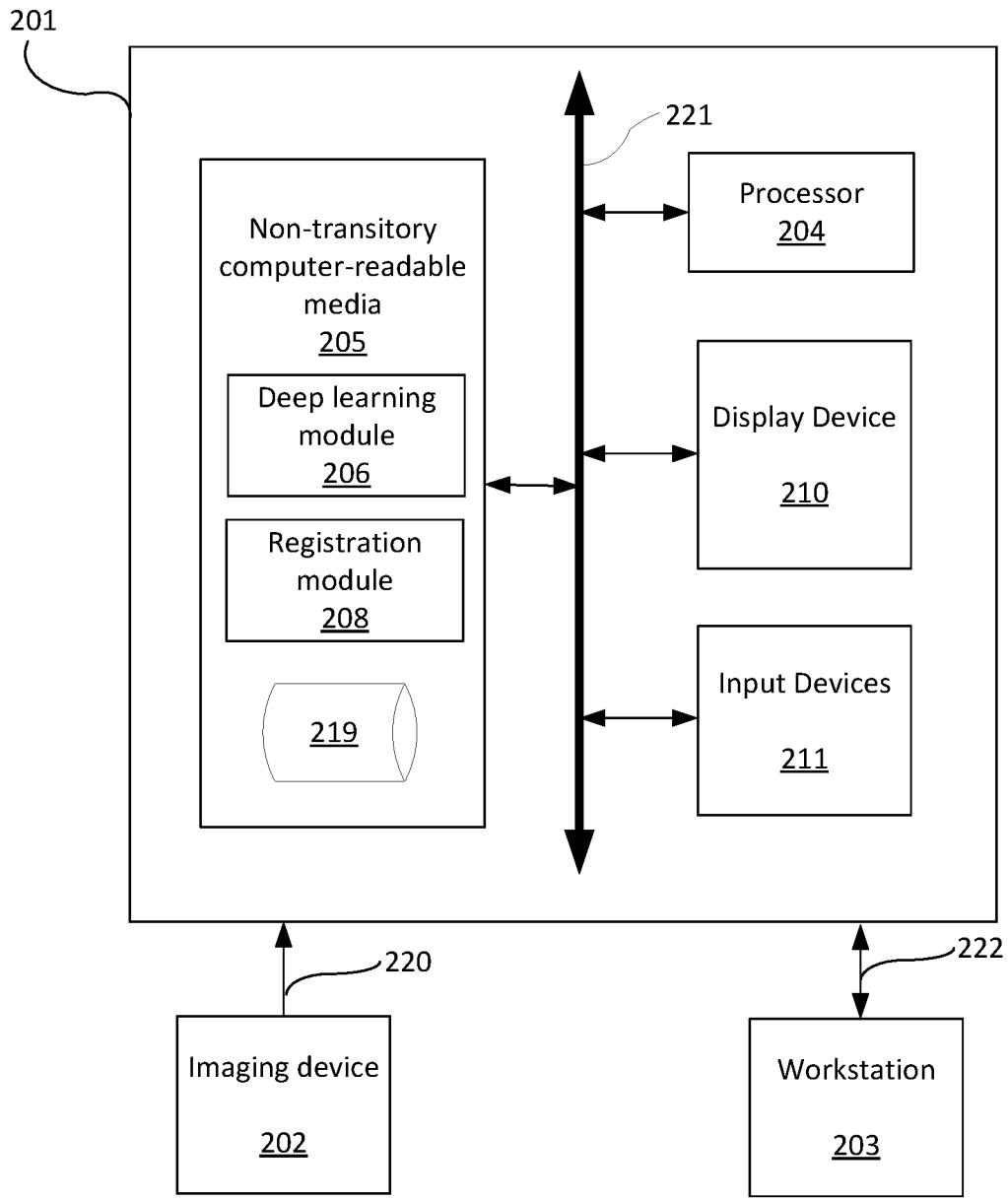
FIG. 2 is a block diagram illustrating an exemplary system.

FIG. 2 is a block diagram illustrating an exemplary system 200. The system 200 includes a computer system 201 for implementing the framework as described herein. In some implementations, computer system 201 operates as a standalone device. In other implementations, computer system 201 may be connected (e.g., using a network) to other machines, such as imaging device 202 and workstation 203. In a networked deployment, computer system 201 may operate in the capacity of a server (e.g., thin-client server), a cloud computing platform, a client user machine in server-client user network environment, or as a peer machine in a peer-to-peer (or distributed) network environment.

In some implementations, computer system 201 comprises a processor 204 (e.g., central processing unit (CPU) or graphics processing unit (GPU)) coupled to one or more non-transitory computer-readable media 205 (e.g., computer storage or memory), display device 210 (e.g., monitor) and various input devices 211 (e.g., mouse or keyboard) via an input-output interface 221. Computer system 201 may further include support circuits such as a cache, a power supply, clock circuits and a communications bus. Various other peripheral devices, such as additional data storage devices and printing devices, may also be connected to the computer system 201.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 205. In particular, the present techniques may be implemented by deep learning module 206, registration module 208 and database 219.

Non-transitory computer-readable media 205 may include random access memory (RAM), read-only memory (ROM), magnetic floppy disk, flash memory, and other types of memories, or a combination thereof. The computer-readable program code is executed by processor 204 to process medical data retrieved from, for example, database 219. As such, the computer system 201 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 205 may be used for storing a database (or dataset) 219. Such data may also be stored in external storage or other memories. The external storage may be implemented using a database management system (DBMS) managed by the processor 204 and residing on a memory, such as a hard disk, RAM, or removable media. The external storage may be implemented on one or more additional computer systems. For example, the external storage may include a data warehouse system residing on a separate computer system, a cloud platform or system, a picture archiving and communication system (PACS), or any other hospital, medical institution, medical office, testing facility, pharmacy or other medical patient record storage system.

Imaging device 202 acquires medical images 220 associated with at least one patient. Such medical images 220 may be processed and stored in database 219. Imaging device 202 may be a radiology scanner and/or appropriate peripherals (e.g., keyboard and display device) for acquiring, collecting and/or storing such medical images 220. In some implementations, the radiology scanner is a hybrid imaging system (e.g., PET/CT or SPECT/CT scanner) that acquires functional images along with anatomical images.

The workstation 203 may include a computer and appropriate peripherals, such as a keyboard and display device, and can be operated in conjunction with the entire system 200. For example, the workstation 203 may communicate directly or indirectly with the imaging device 202 so that the medical image data acquired by the imaging device 202 can be rendered at the workstation 203 and viewed on a display device. The workstation 203 may also provide other types of medical data 222 of a given patient. The workstation 203 may include a graphical user interface to receive user input via an input device (e.g., keyboard, mouse, touch screen voice or video recognition interface, etc.) to input medical data 222.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 3:
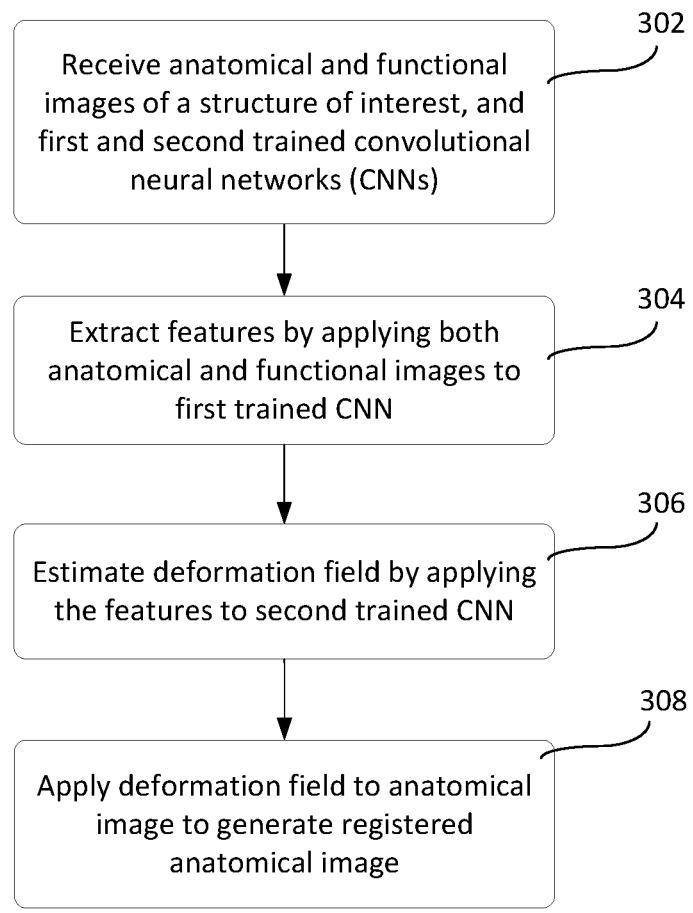
FIG. 3 shows an exemplary method of image registration by a computer system.

FIG. 3 shows an exemplary method 300 of image registration by a computer system. It should be understood that the steps of the method 300 may be performed in the order shown or a different order. Additional, different, or fewer steps may also be provided. Further, the method 300 may be implemented with the system 201 of FIG. 2, a different system, or a combination thereof.

At 302, registration module 208 receives anatomical and functional images of a structure of interest, as well as first and second trained convolutional neural networks (CNNs). The structure of interest may be, for example, a whole body of a patient or a portion thereof (e.g., chest, head, heart). The anatomical image and its corresponding functional image may be retrieved from, for example, database 219 and/or acquired by imaging device 202 from a patient. The anatomical image (e.g., CT, MR) provides structural details, while the functional image (e.g., PET, SPECT) provides insight into biological behaviors, such as changes in metabolism, blood flow, regional chemical composition, or absorption.

The first and second trained convolutional neural networks (CNNs) may be received from deep learning module 206. A CNN is a class of deep, feed-forward artificial neural network that uses a variation of multilayer perceptrons designed to require minimal preprocessing. In some implementations, the first and second CNNs are based on spatial transformer networks. See, for example, Jaderberg, M., K. Simonyan, and A. Zisserman, *Spatial transformer networks*, Advances in neural information processing systems, 2015. 28: p. 2017-2025, which is herein incorporated by reference.

Deep learning module 206 trains the first and second CNNs by using a training image dataset of the structure of interest. In some implementations, the entire population of training images is first reviewed to ensure only pairs of functional and anatomical images with good natural alignment are used. Cases with substantial spatial deviations may be removed from the training image dataset and reserved for testing. During training, three-dimensional (3D) patches may be extracted from the training images for input into the CNNs for training. Within each functional-anatomical image patch pair, artificial mis-registrations may be imposed through random affine and elastic transformations independently performed on both inputs. In this way, the pair's relative deformation may be known and used as the target label in a supervised training task.

The entire network may be trained end-to-end in a supervised fashion. The pixel-wise mean squared error (MSE) between the network output and deformation target may be the loss function, and minimized using the Adam optimizer. See, for example, Kingma, D. P. and J. Ba, Adam: *A method for stochastic optimization*, arXiv preprint arXiv: 1412.6980, 2014, which is herein incorporated by reference. Performance of the registration may be continually monitored within the training set, as well as in the independent testing population.

Figure 4:
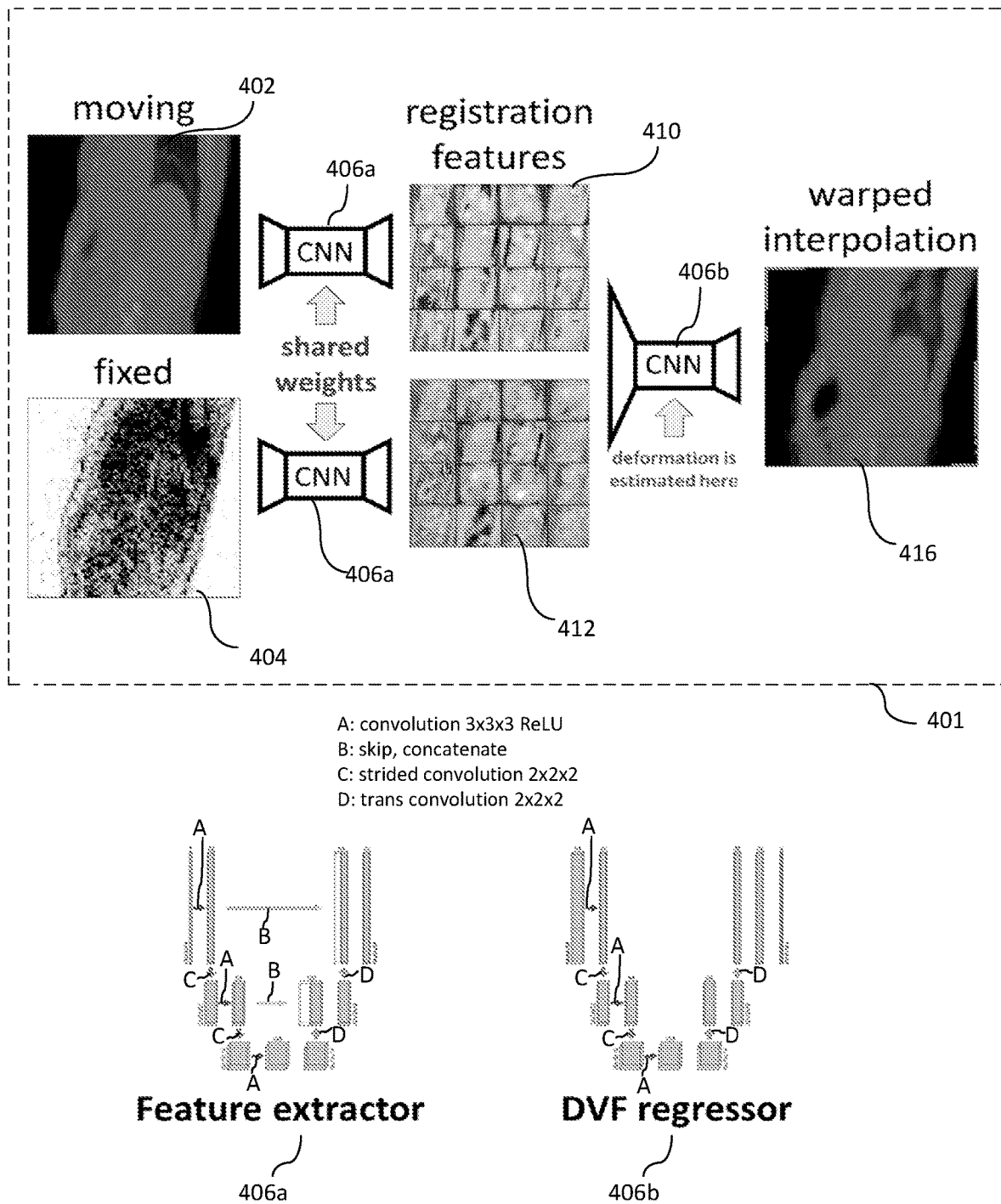
FIG. 4 shows an exemplary registration framework.

Returning to FIG. 3, at 304, registration module 208 extracts features by applying both the anatomical and functional images as input to the first trained CNN. Features are parts or patterns of a structure in an image that can be used for subsequent registration. FIG. 4 shows an exemplary registration framework 401. The registration framework 401 may include separable first CNN 406a and second CNN 406b that receives as input anatomical image 402 and functional image 404. Input anatomical image 402 is the moving image to be deformed to align with input functional image 404 (i.e., fixed or reference image). The first network 406a may be applied equivalently (i.e., with the same weights and other network parameters) to the input anatomical and functional images (402, 404) individually. First CNN 406a transforms anatomical image 402 and functional image 404 into first and second feature maps 410 and 412 respectively.

In some implementations, the first CNN 406a includes a feature extractor. Feature extractor 406a may use a modified U-Net configuration, with an encoder-decoder architecture that has contracting and expanding paths connected by layer map concatenation at each resolution block. As illustrated in FIG. 4, each box of the feature extractor 406a in the U-Net configuration corresponds to a multi-channel feature map. The arrows denote different operations A, B, C and D. The modified U-Net configuration of the feature extractor 406a includes a contracting path (left side) and an expansive path (right side). The contracting path includes repeated application of a 3×3×3 convolution followed by a rectified linear unit (ReLU) (operation A) and a 2×2×2 max pooling operation with stride 2 for down sampling (operation C). At each down sampling step, the number of feature channels is doubled. Every step in the expansive path includes an up sampling of the feature map followed by a 2×2×2 convolution (operation D) that halves the number of feature channels, and a concatenation with the correspondingly cropped feature map from the contracting path (operation B). The same network parameters may be used to process every input, and the output feature maps may be produced at the original resolution without any down sampling.

Returning to FIG. 3, at 306, registration module 208 estimates a deformation field using the second trained CNN. The deformation field may be determined by regressing a relative motion displacement matrix between the anatomical and functional images, and defining an interpolation grid based on the relative motion displacement matrix. The interpolation grid may be represented by a deformation vector field (DVF). Other representations are also possible.

Referring to FIG. 4, second CNN 406b receives as input the sets of feature maps (410, 412) generated based on both original input images (402, 404), and produces a three-dimensional (3D) deformation vector field (DVF) 416 characterizing the relative deformation of the pair of images. In some implementations, second CNN 406b includes a DVF regressor that regresses the relative motion displacement matrix between the input anatomical and functional images (402, 404). DVF regressor 406b may use an encoder-decoder architecture similar to the feature extractor 406a, but without the skip connections between encoding and decoding paths (operation B). DVF regressor 406b accepts as input the concatenated output feature maps (410, 412) and regresses the relative displacement field between them to generate the output DVF 416. The output DVF 416 quantitatively characterizes the deformation field, and can be used to subsequently resample the moving image 402.

At 308, registration module 208 applies the deformation field to the anatomical image to generate a registered anatomical image. The deformation field may be applied by resampling or interpolating the anatomical image (or moving image) using the interpolation grid (e.g., DVF). The registered anatomical image may then be used for functional image correction and reconstruction. For example, the registered anatomical image may be used to generate an attenuation coefficient map (i.e., mu map) for correcting raw acquisition data (e.g., PET data) for attenuation and scatter. Functional images may then be reconstructed based on the mu map.

The effects on PET image reconstruction of spatially registered attenuation correction (AC) data were investigated. The evaluation of this study is presented in the context of comparison with the default method, and so PET images were reconstructed both ways: with a warped mu map (wPET) and with the original, unmodified mu map (oPET). Images were compared, and qualitative findings are illustrated for different scenarios, including a specific focus on respiratory motion. For the whole body (WB) data, the total amounts of quantified tracer activity in the reconstructed PET images were measured and compared. A 2-tailed, paired t-test was used to determine if the differences were significant between the methods.

The warped anatomical image was used to generate the subject mu map for the PET reconstruction, and the wPET image was quantitatively compared to the oPET image. This process was repeated for all test subjects. Matching the mu map to the PET data was found to yield reconstructed PET images with generally higher quantified tracer activity. The mean activities measured within the whole body were 67.3 MBq and 68.5 MBq for the oPET and wPET images, respectively. The paired t-test determined that these population differences were statistically significant (1.2±0.99 MBq, p=0.002).

Figure 5:
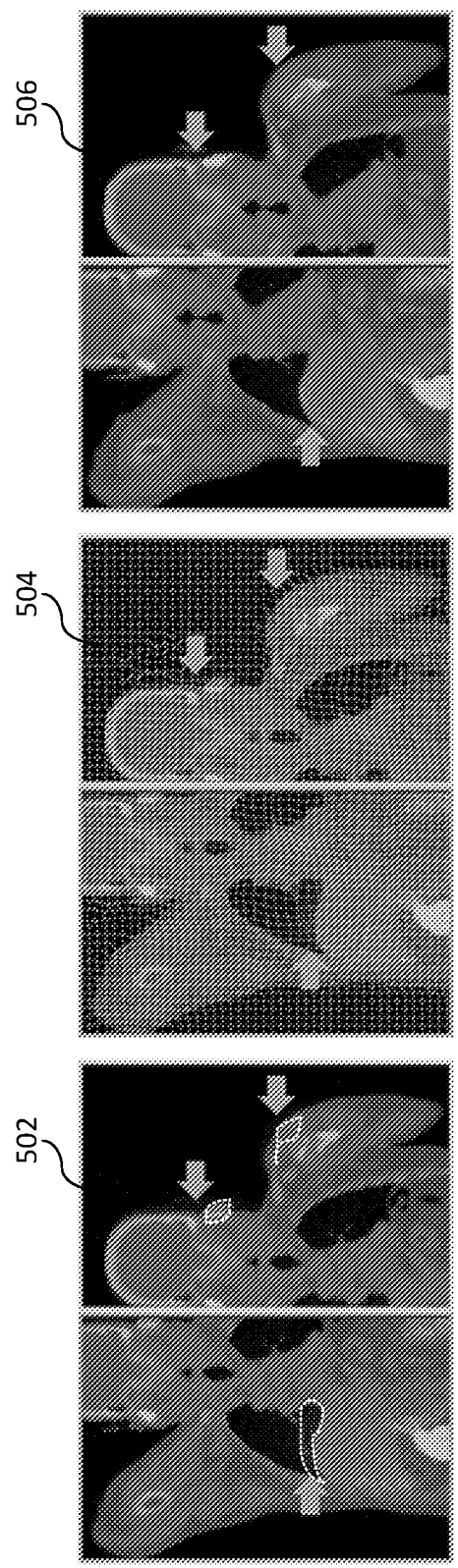
FIG. 5 shows exemplary registration results.

FIG. 5 shows exemplary registration results. PET reconstruction artifacts (delineated by broken lines) due to respiratory and bulk motion are displayed in the image 502 at locations indicated by the arrows. The DVF predicted by the CNNs is overlayed in the image 504, and the CT image 506 resampled using this DVF is shown. The non-attenuation corrected (NAC) PET image is identical in each display. As shown, artifacts at the locations indicated by the arrows were minimized or eliminated in the resampled image 506.

Figure 6:
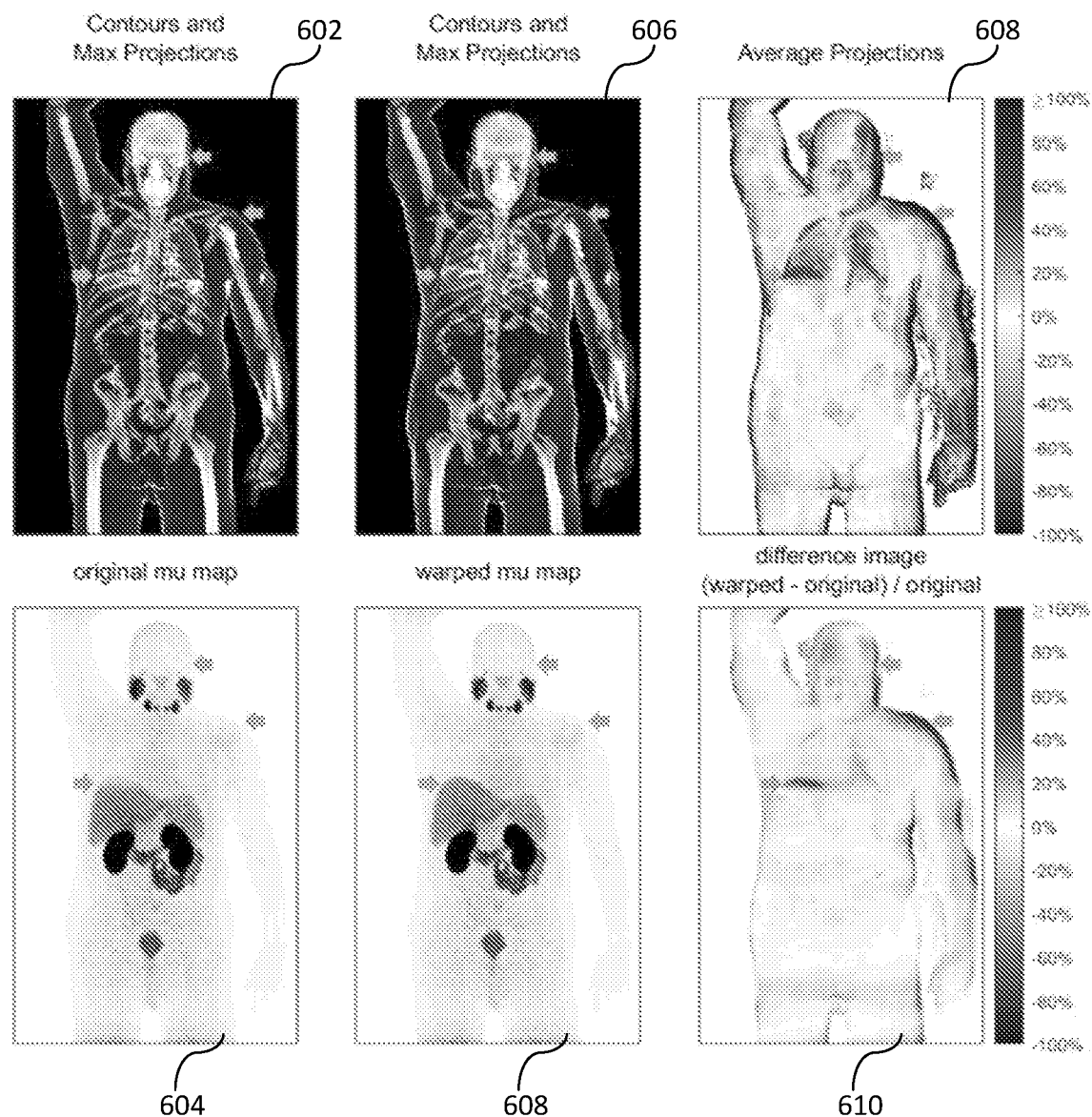
FIG. 6 shows an exemplary whole-body overview of a validation subject.

FIG. 6 shows an exemplary whole-body overview of a validation subject. Original mu map 604 and warped mu map 608 are shown with their corresponding PET images 602 and 606 respectively, along with the average projection map 608 and relative difference image 610. The relative difference image 610 is determined by subtracting the original mu map 604 from the warped mu map 608, and dividing the subtraction result by the original mu map 608. Using the warped mu map 608 to match the PET activity recovered approximately 1% additional tracer activity in the reconstructed image across the whole body. Fewer respiratory artifacts were observed. The subject additionally showed clear improvement for bulk motion artifacts in the arms.

Figure 7:
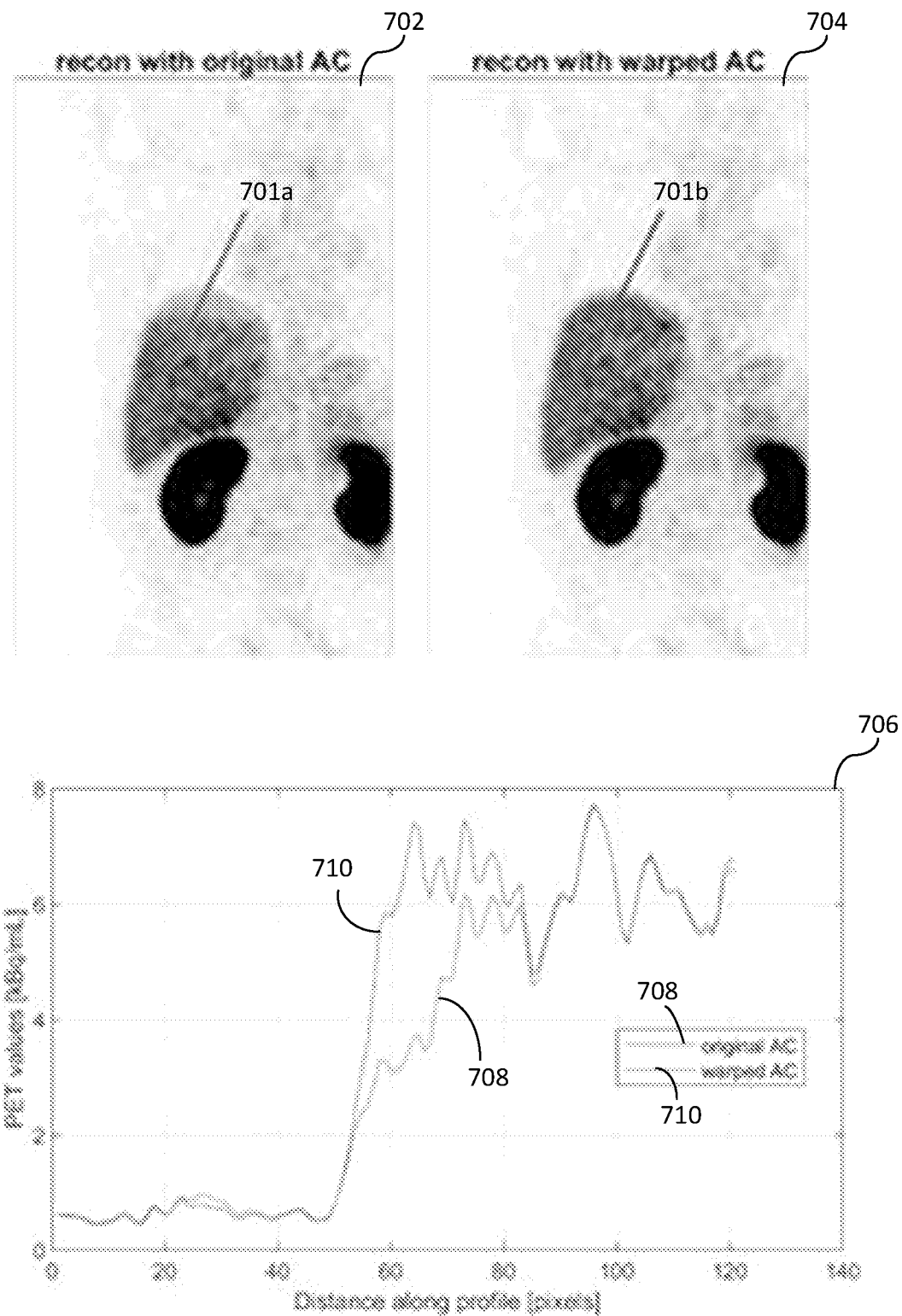
FIG. 7 shows exemplary line profiles drawn over a site with large respiratory motion on both original PET (oPET) image and warped PET (wPET) image.

FIG. 7 shows exemplary line profiles 701a-b drawn over a site with large respiratory motion on both oPET image 702 and wPET image 704. Graph 706 shows the reconstructed PET activity values 708 and 710 along line profiles 701a and 701b respectively. The wPET image 704 demonstrated a clear improvement over oPET image 702 for the respiratory artifact. Quantified activity was recovered at the liver dome, producing more uniform reconstructed tracer distribution within the organ. This example illustrates a potentially significant benefit of spatially registering the mu map to the PET data—the artifact was largely corrected, producing more accurately quantified liver uptake.

The wPET image 704 shows significantly higher reconstructed activity values at the edges of the head and left shoulder, presumably from misalignments due to gross subject motion. Involuntary physiological motion also causes spatial mismatches, and a closer look at the region surrounding the lung-liver boundary shows one such resulting respiratory artifact in the oPET image, in which the top of the liver is not fully corrected.

Respiratory artifacts like the one shown in FIG. 7 occur when the CT is acquired in a state of deeper inspiration relative to the average respiratory cycle and are extremely common in PET imaging. Indeed, such discrepancies were observed in most of the testing data sets—the corresponding artifacts were found to be systematically improved in the wPET images.

Figure 8:
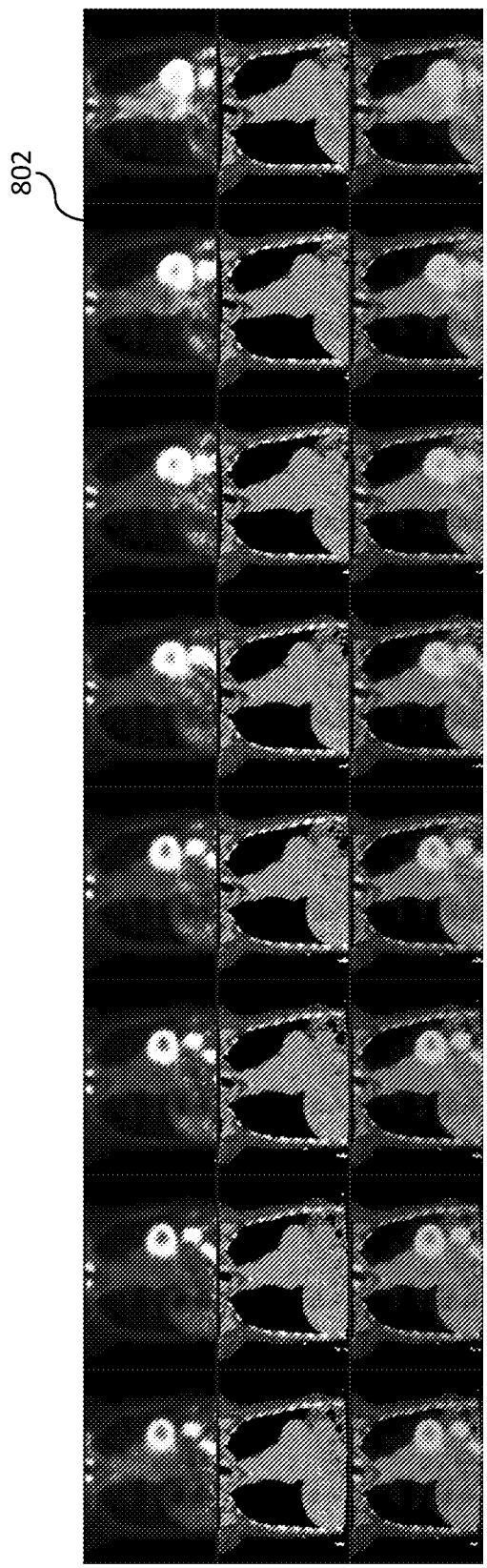
FIG. 8 shows an exemplary gated PET/CT series for a 82Rb cardiac perfusion subject.

FIG. 8 shows an exemplary gated PET/CT series 802 for a 82Rb cardiac perfusion subject. Myocardial (or cardiac) perfusion is a nuclear stress test that is performed to show how well blood flows through the heart muscle. For each of the respiratory PET phases, the same CT was warped to match the tracer distribution of the PET frame. This subject exhibited a relatively large range of respiratory motion, and the registration successfully aligned the liver dome and heart between the PET and CT for all 8 physiological frames.

For the cardiac perfusion application, the registration CNN was initialized with the learned parameters from the WB network. It was then trained for 6000 additional iterations on the single-bed cardiac data until the losses converged and acceptable performance was observed in the validation subjects. FIG. 8 shows the registration results for optimizing the attenuation correction at every frame of a gated study. To best illustrate this, a single cardiac test subject exhibiting the largest range of respiratory motion was selected, and the 8 respiratory gated PET/CT images are displayed. For each frame, the original CT image was independently warped to match the tracer distribution in each physiological phase. Warping the mu map to the PET data was found to ensure alignment at the liver dome and heart for all physiological frames.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system for image registration, comprising:
    a non-transitory memory device for storing computer readable program code; and
    a processor in communication with the memory device, the processor being operative with the computer readable program code to perform steps including
        receiving an anatomical image and a functional image of a structure of interest, and first and second trained convolutional neural networks,
        extracting features by applying the anatomical image and the functional image as input to the first trained convolutional neural network,
        estimating a deformation field by applying the features as input to the second trained convolutional neural network, wherein the second trained convolutional neural network comprises a deformation vector field regressor that regresses a relative motion displacement matrix between the anatomical image and the functional image, and
        applying the deformation field to the anatomical image to generate a registered anatomical image.

2. The system of claim 1 wherein the anatomical image comprises a computed tomography (CT) or magnetic resonance (MR) image.

3. The system of claim 1 wherein the functional image comprises a Positron Emission Tomographic (PET) or a single-photon emission computed tomography (SPECT) image.

4. The system of claim 1 wherein the first trained convolutional neural network comprises a feature extractor that uses a modified U-Net configuration.

5. The system of claim 1 wherein the deformation vector field regressor uses an encoder-decoder architecture.

6. A method for image registration, comprising:
receiving an anatomical image and a functional image of a structure of interest, and first and second trained convolutional neural networks;
extracting features by applying the anatomical image and the functional image as input to the first trained convolutional neural network;
estimating a deformation field by applying the features as input to the second trained convolutional neural network, wherein the second trained convolutional neural network comprises a deformation vector field regressor that regresses a relative motion displacement matrix between the anatomical image and the functional image; and
applying the deformation field to the anatomical image to generate a registered anatomical image.

7. The method of claim 6 wherein the anatomical image comprises a computed tomography (CT) or magnetic resonance (MR) image.

8. The method of claim 6 wherein the functional image comprises a Positron Emission Tomographic (PET) or a single-photon emission computed tomography (SPECT) image.

9. The method of claim 6 further comprises performing training using pairs of functional and anatomical image patches to generate the first and second trained convolutional neural networks.

10. The method of claim 6 wherein extracting features by applying the anatomical image and the functional image as input to the first trained convolutional neural network comprises using the first trained convolutional neural network equivalently for the anatomical image and the functional image.

11. The method of claim 6 wherein extracting features by applying the anatomical image and the functional image as input to the first trained convolutional neural network comprises applying the anatomical image and the functional image to a feature extractor that uses a modified U-Net configuration.

12. The method of claim 6 wherein the deformation vector field regressor estimates the deformation field by further defining an interpolation grid based on the relative motion displacement matrix.

13. The method of claim 6 wherein the deformation vector field regressor uses an encoder-decoder architecture.

14. The method of claim 6 wherein applying the deformation field to the anatomical image to generate the registered anatomical image comprises resampling the anatomical image using the deformation field.

15. The method of claim 6 further comprises generating an attenuation correction map based on the registered anatomical image for correcting raw acquisition data.

16. The method of claim 15 further comprises correcting the raw acquisition data based on the attenuation correction map and reconstructing one or more images based on the corrected raw acquisition data.

17. The method of claim 6 wherein the anatomical image and the functional image comprise a cardiac perfusion CT image and a PET image respectively.

18. One or more non-transitory computer-readable media embodying instructions executable by machine to perform operations, comprising:
extracting features by applying an anatomical image and a corresponding functional image as input to a first convolutional neural network;
estimating a deformation field by applying the features as input to a second convolutional neural network, wherein the second convolutional neural network comprises a deformation vector field regressor that regresses a relative motion displacement matrix between the anatomical image and the functional image; and
applying the deformation field to the anatomical image to generate a registered anatomical image.

19. The one or more non-transitory computer-readable media of claim 18, wherein the first convolutional neural network comprises a feature extractor that uses a modified U-Net configuration.

20. The one or more non-transitory computer-readable media of claim 18, wherein the deformation vector field regressor uses an encoder-decoder architecture.

* * * * *